(12) United States Patent
Kawashima

(10) Patent No.: US 6,755,791 B2
(45) Date of Patent: Jun. 29, 2004

(54) ULTRASONIC DIAGNOSTIC APPARATUS AND ULTRASONIC DIAGNOSTIC METHOD

(75) Inventor: Tomonao Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/417,943

(22) Filed: Apr. 17, 2003

(65) Prior Publication Data

US 2003/0199756 A1 Oct. 23, 2003

(30) Foreign Application Priority Data

Apr. 17, 2002 (JP) ........................................ 2002-115397

(51) Int. Cl.$^7$ ................................................ A61B 8/14
(52) U.S. Cl. ..................... 600/467; 600/437; 600/443; 600/462; 600/466; 128/899
(58) Field of Search ................................ 600/407–482; 128/899

(56) References Cited

U.S. PATENT DOCUMENTS

| | | | | |
|---|---|---|---|---|
| 5,253,647 | A | * 10/1993 | Takahashi et al. | ........... 600/424 |
| 5,398,691 | A | * 3/1995 | Martin et al. | ................ 600/463 |
| 5,876,345 | A | * 3/1999 | Eaton et al. | ................. 600/466 |
| 5,924,989 | A | 7/1999 | Polz | ............................ 600/443 |
| 6,148,095 | A | * 11/2000 | Prause et al. | ................ 382/131 |
| 6,175,757 | B1 | 1/2001 | Watkins et al. | |
| 6,203,493 | B1 | * 3/2001 | Ben-Haim | ................... 600/117 |
| 6,216,027 | B1 | 4/2001 | Willis et al. | |
| 6,248,074 | B1 | 6/2001 | Ohno et al. | |
| 2002/0052546 | A1 | * 5/2002 | Frantz et al. | ................ 600/424 |

FOREIGN PATENT DOCUMENTS

| | | |
|---|---|---|
| EP | 1 181 893 A1 | 2/2002 |
| JP | 11-123187 | 5/1999 |

OTHER PUBLICATIONS

U.S. patent application Publication No. U.S. 2002/0049375 A1, published Apr. 25, 2002, issued to Strommer et al.

* cited by examiner

Primary Examiner—Dennis W. Ruhl
Assistant Examiner—William C. Jung
(74) Attorney, Agent, or Firm—Scully, Scott, Murphy & Presser

(57) ABSTRACT

An ultrasonic diagnostic apparatus includes one transmitting coil arranged in the longitudinal direction of an endoscope inserting portion in an ultrasonic endoscope, and another transmitting coil for detecting the position and the direction, which detects the position and the direction of a tomographic plane when forming a tomogram at a distal end portion of an inserting portion by an ultrasonic vibrator. A coil energizing signal is applied to both the transmitting coils so as to generate a magnetic field. The magnetic field is detected by receiving coils. A position and direction calculating circuit detects positional data of the one transmitting coil and positional and directional data of the other transmitting coil. The calculated data is transmitted to an auxiliary-image forming circuit which forms an image of an inserting shape and an auxiliary image indicating the position and the direction of the tomographic plane.

20 Claims, 10 Drawing Sheets

ULTRASONIC DIAGNOSTIC APPARATUS AND ULTRASONIC DIAGNOSTIC METHOD

This application claims benefit of Japanese Patent Application No. 2002-115397 filed in Japan on Apr. 17, 2002, the contents of which are incorporated by this reference.

BACKGROUND OF THE INVENTION

1. Field of the Invention

The present invention relates to an ultrasonic diagnostic apparatus and an ultrasonic diagnostic method for ultrasonic diagnosis.

2. Description of the Related Art

Ultrasonic diagnostic apparatuses including an ultrasonic endoscope are well-known as those for diagnosis using an elongated ultrasonic probe which is inserted in the celom.

In the ultrasonic diagnostic apparatuses, in particular, in the ultrasonic endoscope in which an optical observing window is provided for an ultrasonic probe used by being inserted in the celom, an operator normally observes the celom by using an optical image as guide and inserts the distal end of the ultrasonic probe in the celom to a near area of the concerning area such as tumor.

Next, the operator determines the position/direction of a tomographic plane from an anatomical positional relationship based on a positional relationship of the organ displayed on an ultrasonic tomogram on a monitor, and the concerning area is displayed onto the monitor by moving the distal end of the ultrasonic probe in the celom.

However, the above-mentioned method has a problem that the determination which image in the celom is indicated by the observed ultrasonic tomogram requires specialized knowledge about a relation between the ultrasonic tomogram and the anatomia and experiences for operating the ultrasonic probe in the celom and for reading the ultrasonic tomogram.

Further, if the ultrasonic probe is so thin in diameter that image pick-up means of an optical image cannot be provided, the optical image is not used as a guiding one. In this case, the problem becomes serious. In addition, in the case of using the ultrasonic probe in the celom for the deep organ which is not directly observed by using the optical image, such as the pancreas and the bile duct, the optical image is not used as the guiding one and therefore the problem becomes more serious and inhibits the spread of ultrasonic examination in the celom in this field.

Accordingly, Japanese Unexamined Patent Application Publication No. 11-123187 discloses an apparatus which detects the position and direction of an ultrasonic tomogram through an ultrasonic endoscope which is inserted in the celom by using magnetic field and which displays the position and direction as to be an ultrasonic tomographic mark on a body mark such as stomach.

SUMMARY OF THE INVENTION

According to the present invention, an ultrasonic diagnostic apparatus for forming an ultrasonic tomogram based on an ultrasonic echo signal outputted from an ultrasonic probe having an ultrasonic vibrator at a distal end portion thereof and inserted in the celom, comprises an inserting shape detecting portion which detects an inserting shape of the ultrasonic probe, an auxiliary-image forming portion which forms an auxiliary image for correlating the ultrasonic tomogram with the inserting shape obtained by the inserting shape detecting portion, and an output portion which outputs the ultrasonic tomogram and the auxiliary image to a display device so that they can be compared with each other.

Further, according to the present invention, an ultrasonic diagnostic method for forming an ultrasonic tomogram based on an ultrasonic echo signal outputted from an ultrasonic probe having an ultrasonic vibrator at a distal end portion thereof and inserted in the celom, comprises an inserting shape detecting step of detecting an inserting shape of the ultrasonic probe, an auxiliary-image forming step of forming an auxiliary image correlating the ultrasonic tomogram with the inserting shape obtained in the inserting shape detecting step, and an output step of outputting the ultrasonic image and the auxiliary image to a display device so that they can be compared with each other.

The above and other objects, features and advantages of the invention will become more clearly understood from the following description referring to the accompanying drawings.

DESCRIPTION OF THE PREFERRED EMBODIMENTS

Hereinbelow, embodiments of the present invention will be described with reference to the drawings.

First Embodiment

Figure 1:
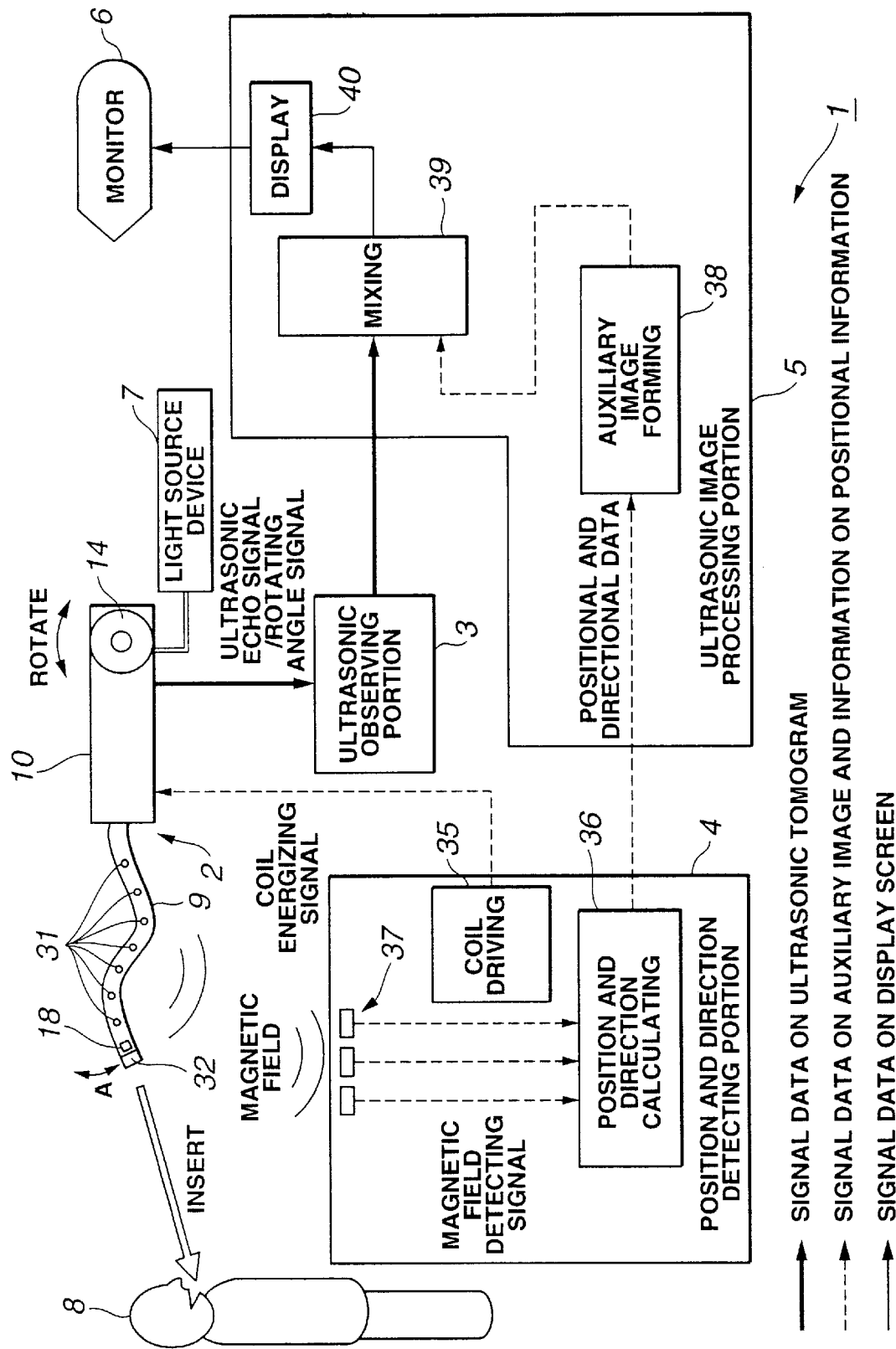
FIG. 1 is a diagram showing the entire structure of an ultrasonic diagnostic apparatus according to a first embodiment of the present invention.
Figure 2:
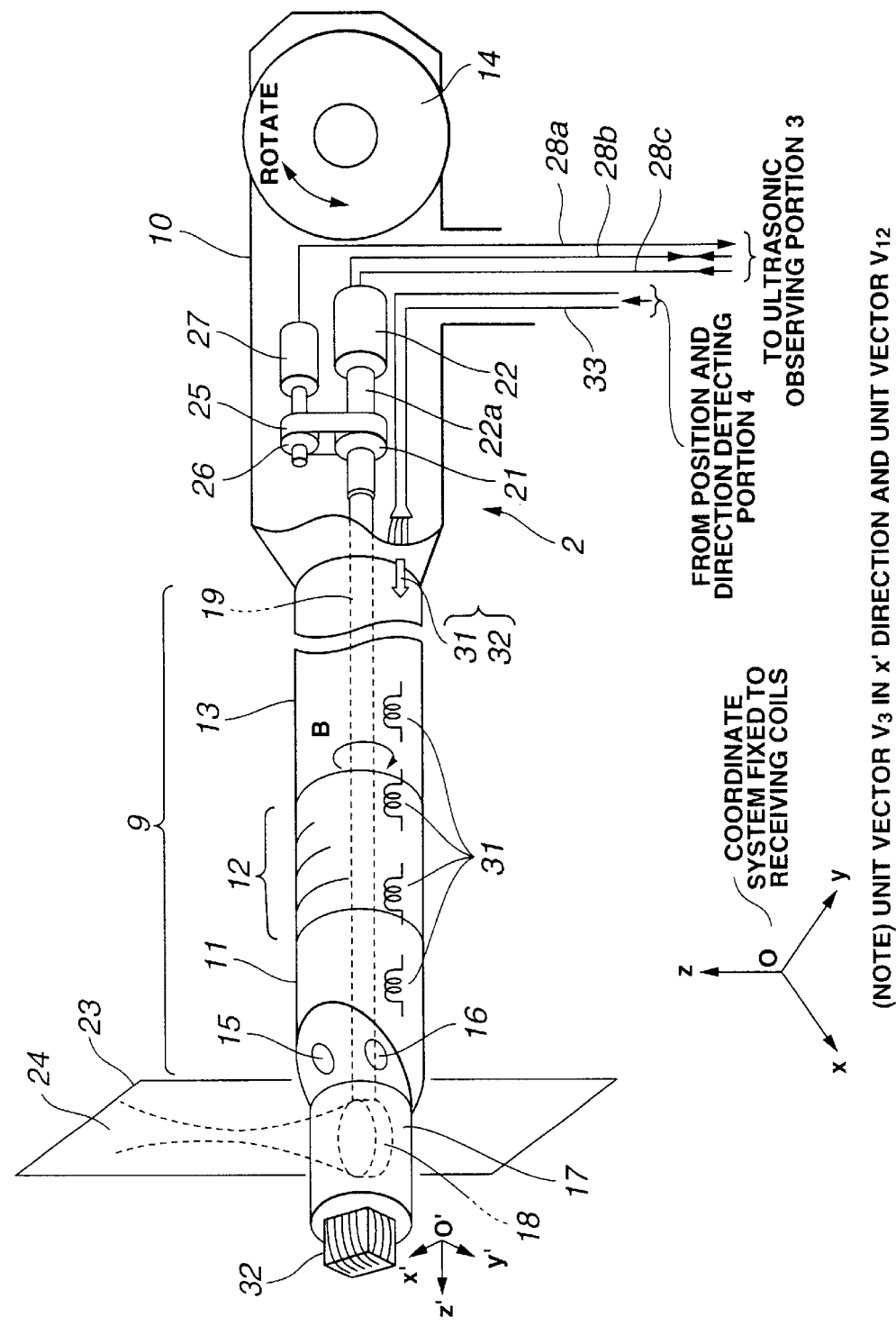
FIG. 2 is an explanatory diagram showing the structure of an ultrasonic endoscope.
Figure 3:
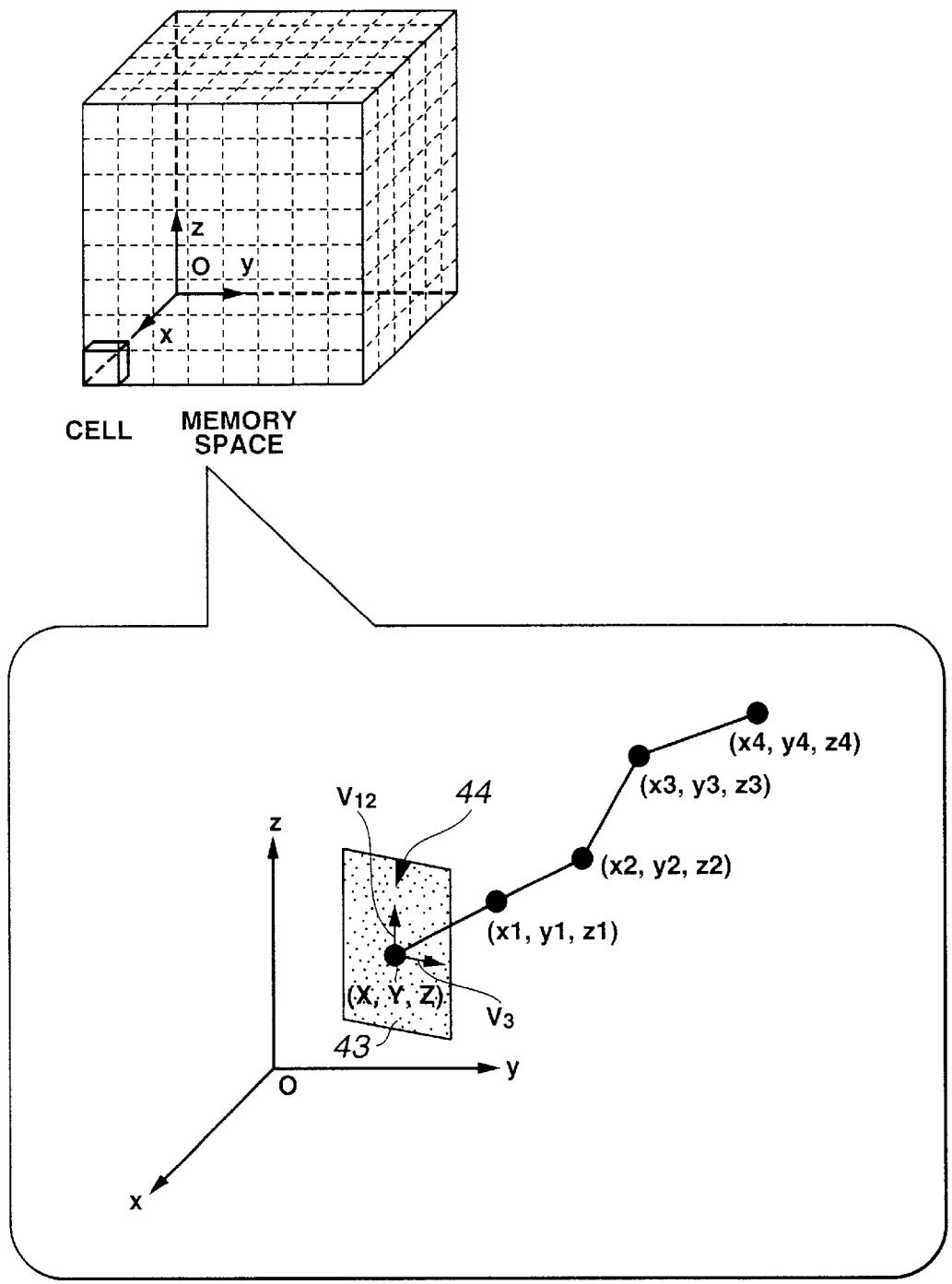
FIG. 3 is an explanatory diagram of the operation of an auxiliary-image forming circuit.
Figure 4:
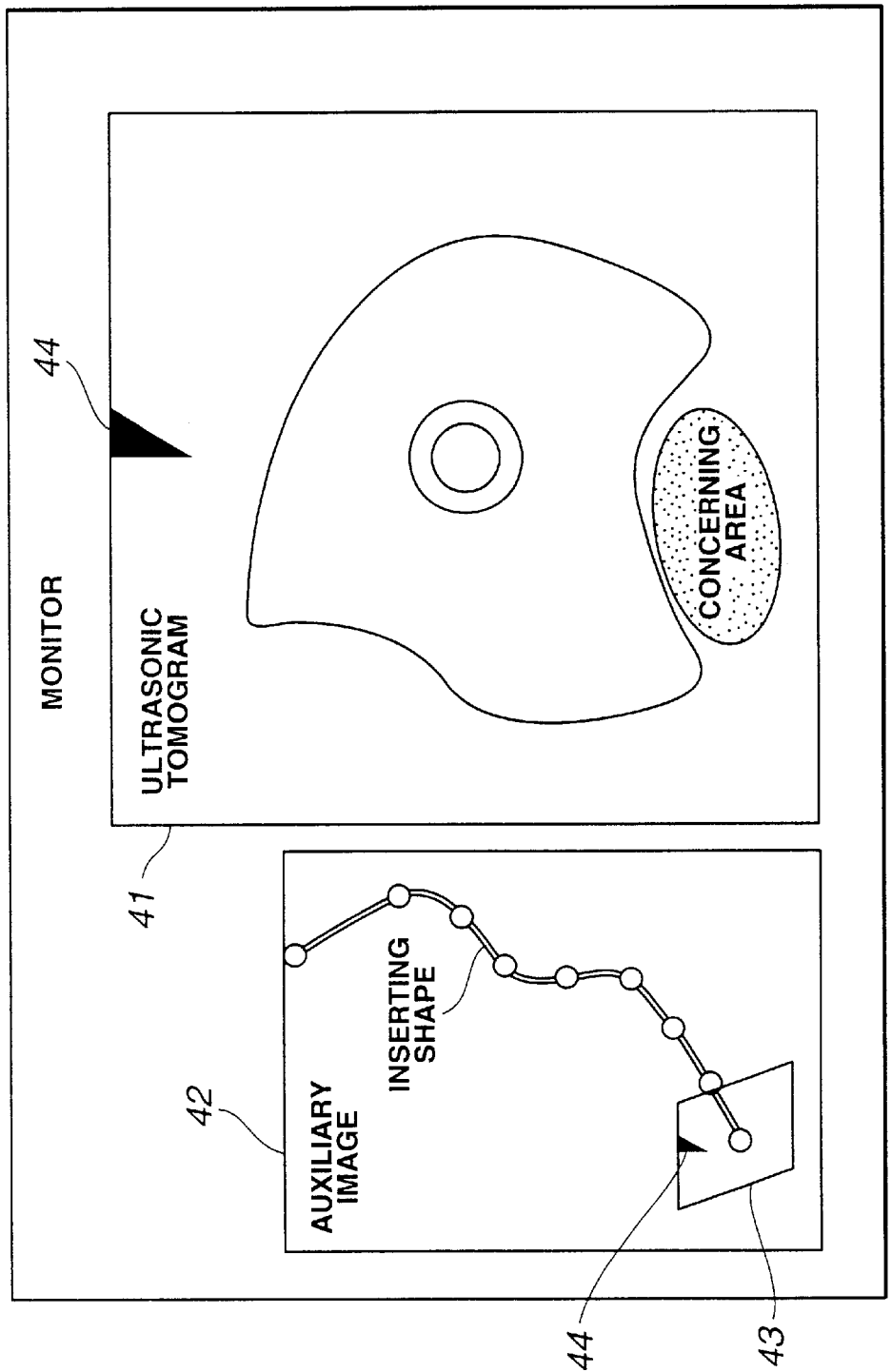
FIG. 4 is an explanatory diagram showing an example of a display screen of an ultrasonic tomogram and an auxiliary image on a monitor.

FIGS. 1 to 4 are diagrams according to a first embodiment of the present invention. FIG. 1 shows the entire structure of an ultrasonic diagnostic apparatus. FIG. 2 shows the structure of an ultrasonic endoscope. FIG. 3 shows an explanatory diagram of the operation of an auxiliary-image forming circuit. FIG. 4 shows an example of a display screen of an ultrasonic tomogram and an auxiliary image on a monitor.

Referring to FIG. 1, an ultrasonic diagnostic apparatus 1 according to the first embodiment of the present invention comprises a radial scanning ultrasonic endoscope (hereinafter, simply referred to as an ultrasonic endoscope) 2 as an ultrasonic probe in the celom, an ultrasonic observing portion 3 which subjects an ultrasonic echo signal obtained by the ultrasonic endoscope 2 to predetermined signal processing and forms an ultrasonic tomogram of a radial scanning plane (hereinafter, simply referred to as a tomographic plane), a position and direction detecting portion 4 which detects a position and a direction of the tomographic plane and an inserting shape of the ultrasonic endoscope 2 by using magnetic field, an ultrasonic image processing portion 5 which forms an auxiliary image showing which image in the celom is indicated by the ultrasonic tomogram based on the position and the direction of the tomogram and the inserting shape and which generates a video signal for simultaneously or switchingly displaying the ultrasonic tomogram and the auxiliary image, a monitor 6 which displays the ultrasonic tomogram and the auxiliary image, and a light source device 7 which generates illumination light for optical observation by using the ultrasonic endoscope 2.

Mainly, the ultrasonic endoscope 2 mainly comprises an endoscope inserting portion 9 which is inserted to a subject 8 and an endoscope operating portion 10 which is arranged at the back end of the endoscope inserting portion 9 and is gripped. The endoscope inserting portion 9 in the ultrasonic endoscope 2 is made of a flexible material because it is inserted in a body cavity having many bending portions, such as the stomach, the esophagus, and the colon in the subject 8.

Specifically, referring to FIG. 2, the endoscope inserting portion 9 comprises a hard distal portion 11 which is arranged at the distal end, a bending portion 12 which is arranged at the back end of the distal end portion 11 and is freely bent, and a flexible portion 13 which is flexible with a long length from the back end of the bending portion 12 and the front end of the endoscope operating portion 10. A bending knob 14 arranged to the endoscope operating portion 10 is rotated, then, a conductor (not shown) inserted in the endoscope inserting portion 9 advances or returns, and the bending portion 12 is bent in a bending direction shown by reference numeral A in FIG. 1. Thus, a user remote-controls the direction of the distal end portion 11.

At the distal end portion 11 of the endoscope, as means for optically observing the subject 8, an illuminating window 15 and an optical observing window 16 are formed at a slope portion which is created like cutting a cylinder on the cross. A light guide (not shown) getting through the endoscope inserting portion 9, etc. is inserted in the illuminating window 15 transfers illumination light from the light source device 7 arranged outside, outputs the illumination light from the illuminating window 15, and illuminates the celom.

The optical image of the concerning portion such as an illuminated affected-part in the celom is formed through an objective optical system attached to the optical observing window 16. Then, the optical image is transferred through the image guide so that it is optically observed via an eyepiece (not shown) provided at the back end of the endoscope operating portion 10. In the arrangement with an image pick-up device such as a CCD which is placed at the image forming position of the objective optical system, a signal picked-up by the image pick-up device is connected to an external video processor, is converted into a video signal, and is displayed on a monitor (not shown).

A cylinder distal cap 17 is set in front of the distal end portion 11 which accommodates, e.g., a disc-shaped ultrasonic vibrator 18. The ultrasonic vibrator 18 is freely rotatably supported by a shaft bearing portion (not shown) on the proximal end side of the distal end cap 17. The shaft bearing portion is connected to a flexible shaft 19 which is inserted in the endoscope inserting portion 9 on the back side. The flexible shaft 19 is connected to a rotary shaft 22a of a motor 22 for rotatably driving via a roller 21 in the endoscope operating portion 10.

The rotation of the motor 22 rotates the flexible shaft 19 as shown by reference numeral B in FIG. 2, and further rotates the ultrasonic vibrator 18 attached on the distal end of the flexible shaft 19. Then, ultrasonic beams 24 are radially outputted on a plane of a tomographic plane 23 vertical to the axis of the endoscope inserting portion 9 shown in FIG. 2, that is, mechanical radial scanning is performed.

The one roller 21 is connected to another roller 26 by a rotary belt 25, and the amount of rotation of the motor 22 is detected by a rotary encoder 27 attached to the rotary axis of the other roller 26.

Specifically, one rotation of the motor 22 causes one-rotation of the one roller 21 and the other roller 26 having the same radius as that of the roller 21. The rotary encoder 27 for detecting the one-rotation detects a rotating angle of the motor 22, and a rotating angle of the ultrasonic vibrator 18 is detected based on the detection of the rotating angle of the motor 22.

A detecting signal of the rotary encoder 27, as a rotating angle signal of the ultrasonic vibrator 18, is transmitted to the ultrasonic observing portion 3 via a signal line 28a.

The ultrasonic vibrator 18 is connected to a signal line which is inserted into the flexible shaft 19. This signal line becomes a signal line 28b externally extending from the motor 22, and is connected to the ultrasonic observing portion 3. The signal line 28b applies a transmission driving signal to the ultrasonic vibrator 18, and sends to the ultrasonic observing portion 3, the ultrasonic echo signal which is received by the ultrasonic vibrator 18 and converted into an electrical signal.

Further, the motor 22 is connected to the ultrasonic observing portion 3 via a signal line 28c so as to control rotational driving B and control the stop of rotation.

Furthermore, according to the first embodiment, a plurality of transmitting coils 31 for detecting an inserting shape (hereinafter, referred to as transmitting coils 31) are provided at a predetermined interval in the axial direction of the endoscope inserting portion 9 so as to detect the inserting shape of the endoscope inserting portion 9.

The transmitting coils 31 are solenoid coils which are wound by wirings around one axis, and the winding direction of the transmitting coils 31 are in parallel with the axis of the endoscope inserting portion 9. When the endoscope inserting portion 9 is inserted in the subject 8, it is fixed in the endoscope inserting portion 9 so that it moves integrally with the endoscope inserting portion 9.

Further, according to the first embodiment, a transmitting coil 32 for detecting the position and direction of the tomographic plane, which detects the position and direction of the tomographic plane 23 (hereinafter, referred to as a transmitting coil 32 for detecting the position and direction), is attached at the distal position of the distal end cap 17.

The transmitting coil 32 for detecting the position and the direction is formed integrally with the two solenoid coils formed by winding wirings around two orthogonal axes. For the convenience, the transmitting coil 32 for detecting the position and direction is fixed such that two directions (directions x' and y' in FIG. 2) vertical to an inserting axis (in a direction z' in FIG. 2) of the endoscope inserting portion 9 match the coil winding direction. It is assumed that the direction x' corresponds to a three-o'clock direction of the ultrasonic tomogram and the direction y' corresponds to a twelve-o'clock direction of the ultrasonic tomogram.

The transmitting coil 32 for detecting the position and direction and the transmitting coils 31 are connected to signal lines which are inserted in the endoscope inserting portion 9. These signal lines are bundled in the endoscope operating portion 10 as a cable 33 and are then connected to the position and direction detecting portion 4.

Referring to FIG. 1, the position and direction detecting portion 4 comprises a coil driving circuit 35 which transmits a coil energizing signal to the transmitting coils 31 and the transmitting coil 32 for detecting the position and the direction, a plurality of receiving coils 37 in which their coil winding directions are different so as to detect spatial magnetic field of the transmitting coils 31 and the transmitting coil 32 for detecting the position and the direction (hereinafter, referred to as receiving coils) 37, and a position and direction calculating circuit 36 which calculates positional data (x, y, z) of the plurality of transmitting coils 31, positional data (x, y, z) and directional data (φ, θ, ϕ) of the transmitting coil 32 for detecting the position and the direction based on a magnetic filed detecting signal from the receiving coils 37. Incidentally, the receiving coils 37 are spatially fixed. As shown in FIG. 1, the ultrasonic image processing portion 5 comprises an auxiliary-image forming circuit 38 which forms an auxiliary image based on the positional data of the transmitting coils 31 and the positional data and the directional data of the transmitting coil 32 for detecting the position and the direction, and a mixing circuit 39 which displays the auxiliary image and the ultrasonic tomogram transmitted from the ultrasonic observing portion 3 on the same plane, and a display circuit 40 which converts a mixing output transmitted from the mixing circuit 39 into a video signal and which outputs the video signal on the monitor 6.

Referring to FIG. 1, using various thicknesses of lines, the transmissions and receptions of the data on the ultrasonic tomogram, information on the positional direction, a signal/data on the auxiliary image, and a signal/data on the display screen are indicated. A coordinate system O-xyz fixed to the receiving coils 37 is indicated in FIG. 2.

According to the first embodiment, the inserting shape of the endoscope inserting portion 9 is detected, which will be described later, and it is characterized that the position and direction of the tomographic plane 23 obtained by scanning by the ultrasonic vibrator 18 placed to the distal end portion 11 are detected and both an ultrasonic tomogram 41 and the auxiliary image 42 are displayed as shown in FIG. 4.

Next, the operation of the embodiments will be described.

First, the signal and data on the ultrasonic tomogram will be described.

The ultrasonic vibrator 18 inserted in the celom of the subject 8 electrically and acoustically converts the transmission driving signals like pulses transmitted from a transmitting circuit (not shown) in the ultrasonic observing portion 3, and electro/acoustic transduces the signals into ultrasonic signals.

Then, the ultrasonic vibrator 18 receives and transmits the ultrasonic signals and radially scans them, transduces the ultrasonic echo of the tomographic plane 23 into the electrical signal, and outputs the ultrasonic echo signal to the ultrasonic observing portion 3. The rotary encoder 27 sequentially outputs the rotating angle of the ultrasonic vibrator 18 as the rotating angle signal to the ultrasonic observing portion 3.

The ultrasonic observing portion 3 subjects the obtained ultrasonic echo signal to well-known processing such as envelope detection, logarithm amplification, and A/D conversion. Further, the ultrasonic observing portion 3 performs digital scan converting processing for converting the signal into a signal on an orthogonal coordinate system so as to output digital echo data on a polar coordinate to the monitor 6 based on the rotating angle signal, forms image data of the ultrasonic tomogram, and outputs the formed data to the mixing circuit 39 in the ultrasonic image processing portion 5. The signal passes through the mixing circuit 39 and the display circuit 40, and is outputted to the monitor 6. Then, the ultrasonic tomogram 41 is displayed on the monitor 6 as shown in FIG. 4.

As will be described later, an up-direction marker 44 (an up-direction marker 44 displayed on the auxiliary image 42) is displayed on the ultrasonic tomogram 41 in FIG. 4 so that a reference direction of the up direction is clearly understood by a user upon displaying the ultrasonic tomogram.

Next, a description is given of the information on the positional information and the signal and data on the auxiliary image 42. The coil driving circuit 35 in the position and direction detecting portion 4 outputs the coil energizing signal as an AC signal to the transmitting coils 31 and the transmitting coil 32 for detecting the position and the direction.

A frequency of the coil energizing signal is varied depending on the transmitting coils 31. In the transmitting coil 32 for detecting the position and the direction, frequencies are varied depending on the conductor winding directions. The transmitting coils 31 generate alternating magnetic field which is energized by varied frequencies, around the endoscope inserting portion 9 that is inserted in the subject 8.

On the other hand, the receiving coils 37 attached to the position and direction detecting portion 4 receive the magnetic field which is energized by the transmitting coils 31, and output the magnetic-field detecting signal as the electrical signal to the position and direction calculating circuit 36 in the position and direction detecting portion 4.

The position and direction calculating circuit 36 resolves the magnetic-field detecting signal by the frequency, thereby resolving the frequencies of the transmitting coils 31 and resolving the directions of the conductor winding direction of the transmitting coil 32 for detecting the position and the direction. Thus, the position and direction calculating circuit 36 calculates the following data which is expressed by the coordinate system O-xyz which is fixed to the receiving coils 37. Further, the position and direction calculating circuit 36 outputs the data as the positional and directional data to the auxiliary-image forming circuit 38 in the ultrasonic image processing portion 5.

Positional and directional data;

Positional data of the transmitting coil 32 for detecting the position and direction: (X, Y, Z)

Directional data of the transmitting coil 32 for detecting the position and the direction: (φ, θ, ϕ)

[Reference numerals φ, θ, and ϕ mean the Euler angle indicating inclinations on a coordinate system O-x'y'z' fixed to the transmitting coil 32 for detecting the position and the direction. It is assumed that the position and direction calculating circuit 36 calculates the angles φ, θ, and ϕ such that the coordinate system O-xyz matches the coordinate system O-x'y'z' fixed to the transmitting coil 32 for detecting the position and the direction shown in FIG. 2 when the coordinate system O-xyz fixed to the receiving coils 37 is rotated by the angle φ around the x axis, is further rotated by the angle θ around the y axis, and is furthermore rotated by the angle ϕ.]

Positional data of the transmitting coil 31: $(x_i, y_i, z_i)$

[Reference numeral i denotes a coil number, incidentally, the coil nearest the distal end of the endoscope inserting portion 9 is No. 1]

Then, the auxiliary-image forming circuit 38 forms the auxiliary image which is obtained by combining the inserting shape of the endoscope inserting portion 9 and the position and the direction of the tomographic plane 23 based on the positional and directional data (X, Y, Z), (φ, θ, φ), and (xi, yi, zi), and outputs the auxiliary image to the mixing circuit 39.

The mixing circuit 39 aligns the image data of the ultrasonic tomogram on the right and the auxiliary image on the left side, respectively, and outputs the image data to the display circuit 40. The display circuit 40 converts the aligned image data into the video signal, and outputs it to the monitor 6. The ultrasonic tomogram 41 and the auxiliary image 42 are aligned and displayed on the monitor 6 as shown in FIG. 4.

Next, the operation of the auxiliary-image forming circuit 38 will be described in detail with reference to FIG. 3.

Calculation of the inserting shape:

(1) A memory space comprising cells having an address of the coordinate system O-xyz fixed to the receiving coils 37 is set by using a memory (not shown) provided for the auxiliary-image forming circuit 38. An initial value of data on the memory space is 0 in all the cells.

(2) Data of the cell having the addresses of the positional data (xi, yi, zi) of the transmitting coil 31 and the positional data (X, Y, Z) of the transmitting coil 32 for detecting the position and the direction is 1.

(3) The cells are connected by a line segment in ascending order of coil number i, and data of the cell having the address on the line segment is 1. This connecting method may use a straight line-segment or a spline curve.

(4) The cell having the address of the positional data (xi, yi, zi) of the No. 1 coil (transmitting coil 31 nearest the distal end of the endoscope inserting portion 9) and the cell having the address of the positional data (X, Y, Z) of the transmitting coil 32 for detecting the position and the direction are connected by a line segment similarly to the case (3), and data of the cell having the address on the line segment is 1.

Calculation of position and direction of tomographic plane:

(5) The coordinate x' in FIG. 2 is in the three-o'clock direction of the ultrasonic tomogram, and the coordinate y' is in the twelve-o'clock direction of the ultrasonic tomogram (as to be the reference direction displayed as the up-direction upon display operation). A directional unit vector of the coordinate x' is designated by $V_3$ and a directional unit vector of the coordinate y' is designated by $V_{12}$, components of the vectors $V_3$ and $V_{12}$ on the coordinate system O-xyz fixed to the receiving coils 37 are obtained by the following formulae.

$$\begin{pmatrix} V_3 \ x \ \text{component} \\ V_3 \ y \ \text{component} \\ V_3 \ z \ \text{component} \end{pmatrix} = T_x(\varphi)T_y(\theta)T_z(\phi)\begin{pmatrix} 1 \\ 0 \\ 0 \end{pmatrix} \quad \text{[Formula1]}$$

$$\begin{pmatrix} V_{12} \ x \ \text{component} \\ V_{12} \ y \ \text{component} \\ V_{12} \ z \ \text{component} \end{pmatrix} = T_x(\varphi)T_y(\theta)T_z(\phi)\begin{pmatrix} 0 \\ 1 \\ 0 \end{pmatrix}$$

Herein, a rotating matrix around the x axis is designated by $T_x(\varphi)$, a rotating matrix around the y axis is designated by $T_y(\theta)$, and a rotating matrix around the z axis is designated by $T_z(\phi)$. Then, the rotating matrixes $T_x(\varphi)$, $T_y(\theta)$, and $T_z(\phi)$ are defined as follows.

$$T_x(\varphi) = \begin{pmatrix} 1 & 0 & 0 \\ 0 & \cos\varphi & -\sin\varphi \\ 0 & \sin\varphi & \cos\varphi \end{pmatrix} \quad \text{[Formula2]}$$

$$T_y(\theta) = \begin{pmatrix} \cos\theta & 0 & \sin\theta \\ 0 & 1 & 0 \\ -\sin\theta & 0 & \cos\theta \end{pmatrix}$$

$$T_z(\phi) = \begin{pmatrix} \cos\phi & -\sin\phi & 0 \\ \sin\phi & \cos\phi & 0 \\ 0 & 0 & 1 \end{pmatrix}$$

(6) The three-o'clock direction and the twelve-o'clock direction of the ultrasonic tomogram are obtained on the coordinate system O-xyz fixed to the receiving coils 37 based on the vectors $V_3$ and $V_{12}$. As a result, a parallelogram index (hereinafter, referred to as a tomographic plane marker) 43 as shown in FIG. 3 is generated so as to determine (the position and the direction of) the tomographic plane 23 having the two directions of the vectors $V_3$ and $V_{12}$, the center of which is the cell having the address of the positional data (X, Y, Z) of the transmitting coil 32 for detecting the position and the direction.

Data of the cell having the address within the tomographic plane marker 43 is 0.5. The tomographic plane marker 43 indicates the position and the direction of the tomographic plane of the ultrasonic tomogram.

(7) Further, a triangle index (hereinafter, referred to as the up-direction marker) 44 shown in FIG. 3 is set in the twelve-o'clock direction of the parallelogram. Data of the cell having an address within the up-direction marker 44 is 2.

Completion of auxiliary image:

(8) A modeling is performed on the auxiliary image indicating the inserting shape and the position and direction of the tomographic plane. In the memory space, a portion 0 is not displayed (is transparently displayed), a portion 1 is displayed, a portion 0.5 is displayed (is transparently displayed), and a portion 2 is displayed with a double density. Thus, the auxiliary image is formed to three-dimensionally express the model. The auxiliary image 42 is indicated on the left in FIG. 4.

The following advantages are obtained according to the first embodiment.

With the above-described construction and operation according to the first embodiment, the operation is repeated, thereby sequentially updating and displaying the ultrasonic tomogram 41 every radial scanning of the ultrasonic vibrator 18. The inserting shape in the case and the position and direction of the tomographic plane 23 are combined and are displayed in the auxiliary image 42.

When the operator observes, e.g., the pancreas, the ultrasonic vibrator 18 is inserted in the corpus ventriculus or the duodenum and the pancreas is normally observed through the gastric wall and the intestine wall. According to the first embodiment, the operator moves the distal end of the endoscope inserting portion 9 or changes the direction of the distal end by bending the endoscope inserting portion 9 by the bending knob 14, the inserting shape and the ultrasonic marker 43 are automatically traced, thus to be deformed and be moved. It is easily recognized how the shape of the ultrasonic endoscope 2 is and in which direction the ultrasonic tomogram 41 is observed with respect to the shape of the ultrasonic endoscope 2.

That is, the auxiliary image 42 enables the accomplishment of the above-mentioned object of easily understanding which image in the celom the observed ultrasonic tomogram 41 is.

Since the ultrasonic tomogram 41 is indicated on the auxiliary image 42 as parallelogram (tomographic-plane marker 43) having the sides in the direction $V_3$ (three-o'clock direction) and the direction $V_{12}$ (twelve-o'clock direction), the operator further easily understands in which direction the tomographic plane 23 of the ultrasonic tomogram 41 currently is.

The endoscope inserting portion 9 is screwed so that the parallelogram is in a proper direction or the direction of the distal end is changed by bending the endoscope inserting portion 9 by the bending knob 14. Advantageously, the concerning area is easily imaged.

Further, the marker indicating the twelve-o'clock direction of the ultrasonic tomogram (up-direction marker 44) is provided. Thus, the operator easily understands in which direction the tomographic plane 23 of the ultrasonic tomogram 41 currently is.

The endoscope inserting portion 9 is screwed or the distal end is changed by bending the endoscope inserting portion 9 by the bending knob 14 so that up-direction marker 44 is in the direction of the concerning area. Advantageously, the concerning area is easily imaged.

Modification

According to the first embodiment, the auxiliary image 42 and the ultrasonic tomogram 41 are displayed on the same screen so as to compare them with each other. However, the auxiliary image 42 and the ultrasonic tomogram 41 may be displayed by switching them. Alternatively, they are simultaneously displayed by selecting one of them. Further, they may be displayed on a monitor which is provided separately from them.

For example, the auxiliary image 42 and the ultrasonic tomogram 41 are simultaneously displayed on the same screen. When the observing position and direction of the ultrasonic tomogram 41 are clearly determined, only the ultrasonic tomogram 41 may enlargedly be displayed.

Further, the first embodiment uses the construction for independently arranging the position and direction detecting portion 4, the ultrasonic observing portion 3, the ultrasonic image processing portion 5, and the monitor 6. However, some or all of them may be integrated.

Although the interval between the transmitting coils 31 is set to be constant according to the first embodiment, it may be changed. For example, the interval may be short at a largely bending position, particularly, in or near the bending portion 9 which is bent interlockingly with the bending knob 14.

Further, although the first embodiment uses the ultrasonic endoscope 2 as the radial scanning ultrasonic endoscope for mechanical radial scanning, the present invention may use other scanning methods such as sector scanning or linear scanning.

In addition, the present invention is not limited to the forementioned ultrasonic scanning method and can be applied to the linear scanning which is not vertical but in parallel with the endoscope inserting axis. It may use an ultrasonic probe which does not incorporate the optical observing window 16. Although the first embodiment uses the tomographic plane 23 upon the radial scanning using the radial scanning ultrasonic endoscope as the scanning plane, it may use variously-shaped planes in accordance with various scanning methods.

Although the first embodiment uses the marker in the twelve-o'clock direction (namely, the direction of the vector $V_{12}$) as the marker in the up direction, the present invention is not limited to this. As long as the marker is in a specific direction, it may be, e.g., in the three-o'clock direction (namely, the direction of the vector $V_3$). Further, the marker may be in a plurality of directions and, for example, it may simultaneously be displayed in both the directions of three- and twelve-o'clock.

In addition, the marker may be in the direction of the ultrasonic tomogram which is bent by the bending knob 14. For example, the transmitting coil 32 for detecting the position and the direction may be fixed such that the winding direction of the transmitting coil 32 for detecting the position and the direction matches the bending direction. With the above-described construction, it is apparently understood in which direction the operator should bend the bending knob 14 by changing the direction of the distal end of the endoscope inserting portion 9 so as to view the concerning area.

Therefore, when the pancreas is viewed as the concerning area, the direction of the distal end is changed by bending the bending knob in the direction of the pancreas via the bending knob while viewing the index on the auxiliary image. Thus, advantageously, the concerning area is easily imaged.

The first embodiment uses the parallelogram index as the tomographic plane marker to apparently recognize the vectors $V_3$ and $V_{12}$. However, the tomographic plane marker may use a disk-shaped index or a square-shaped index.

Although the transmitting coil 32 for detecting the position and the direction is constructed by integrating the two solenoid coils which are wound by the conductors around the two orthogonal axes, it may comprise individual coils around the two axes. In this case, the position and direction calculating circuit 36 may correct the positional data (X, Y, Z) of the transmitting coil 32 for detecting the position and the direction such that the data becomes data at a proper position at the distal end of the ultrasonic endoscope 2 by providing an appropriate correcting circuit therefor. Although the receiving coils 37 are constructed by providing the individual solenoid coils in the different directions, they may be an integrate coil.

Second Embodiment

Figure 5:
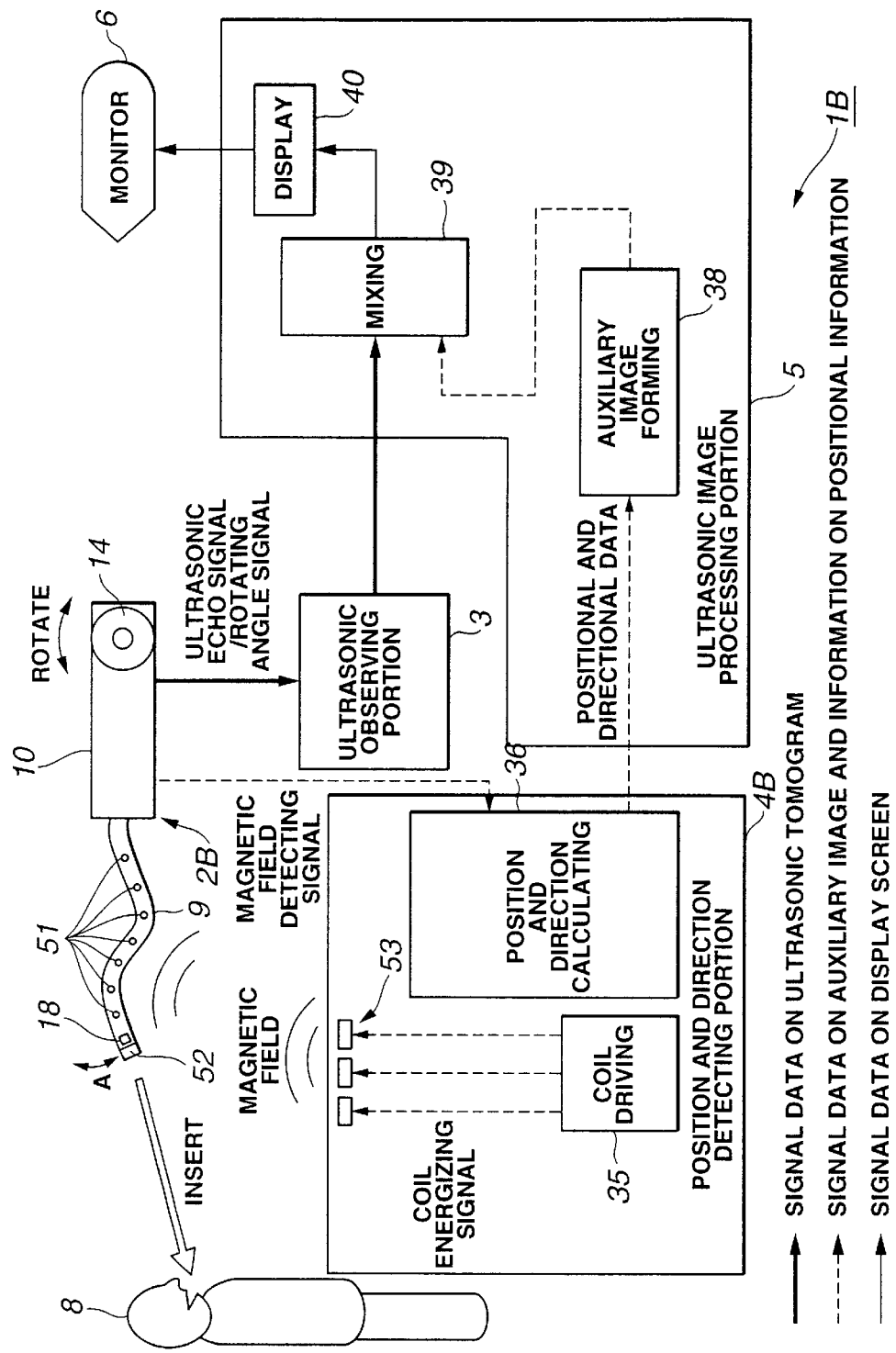
FIG. 5 is a diagram showing the entire structure of an ultrasonic diagnostic apparatus according to a second embodiment of the present invention.
Figure 6:
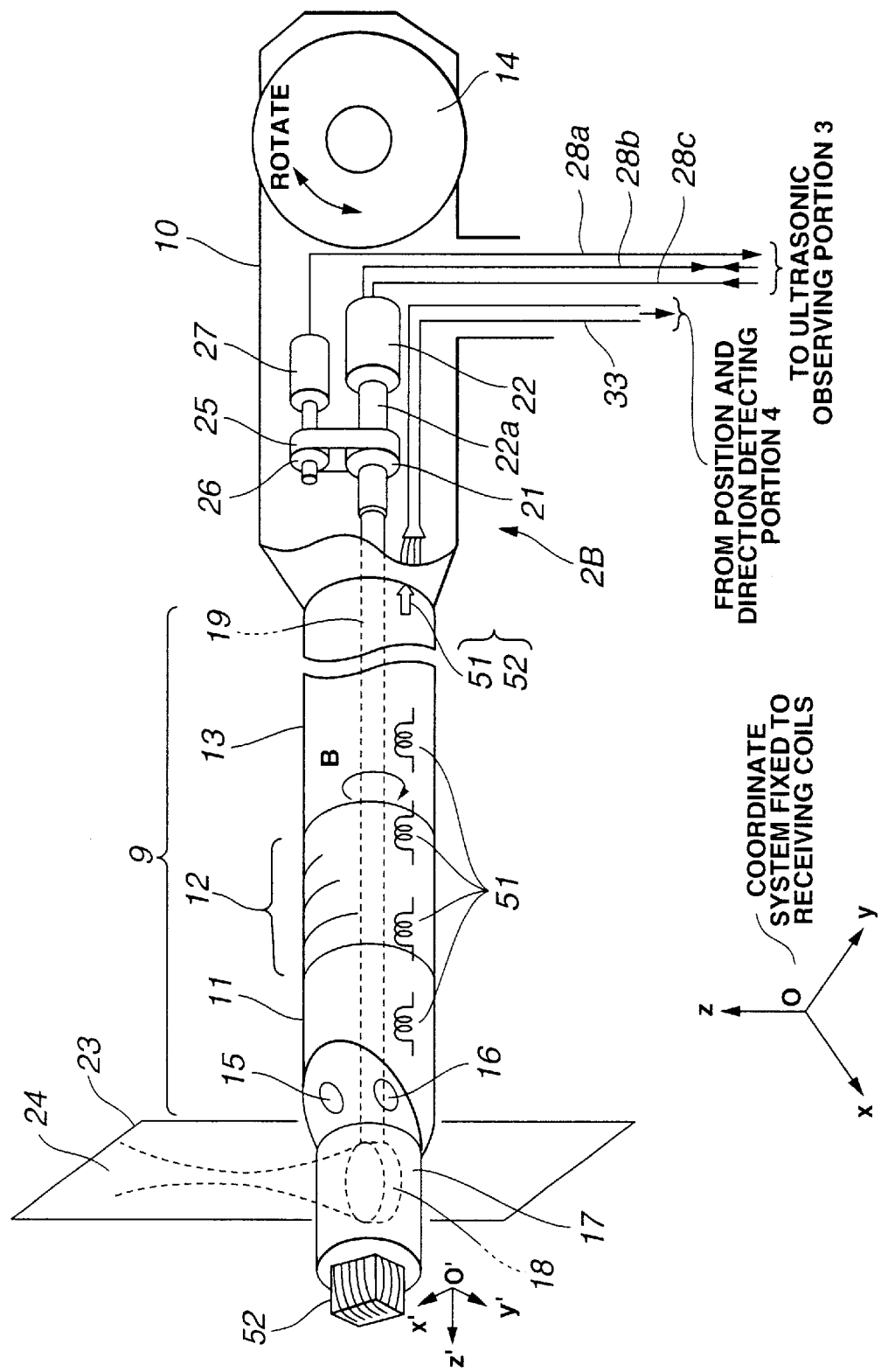
FIG. 6 is an explanatory diagram showing the structure of an ultrasonic endoscope.

Next, a second embodiment of the present invention will be described with reference to. FIGS. 5 and 6. FIG. 5 shows the entire structure of an ultrasonic diagnostic. FIG. 6 shows the structure of an ultrasonic endoscope.

Referring to FIG. 5, according to the second embodiment, an ultrasonic diagnostic apparatus 1B is formed by inverting the relationship between the transmission (generation) and the reception of the magnetic field shown in FIG. 1 according to the first embodiment.

The ultrasonic diagnostic apparatus 1B shown in FIG. 5 has a relationship opposite of that between the transmission and the reception according to the first embodiment.

Specifically, referring to FIG. 6, a plurality of receiving coils for detecting the inserting shape (hereinafter, simply referred to as receiving coils) 51 are arranged to an ultrasonic endoscope 2B according to the second embodiment, in place of the plurality of transmitting coils 31 set in the endoscope inserting portion 9 according to the first embodiment. A receiving coil for detecting the position and the direction of the tomographic plane (hereinafter, referred to as a receiving coil for detecting the position and the position) 52 is attached to the distal end portion, in place of the transmitting coil 32 for detecting the position and direction (of the tomographic plane).

The magnetic field detecting signal which detects the magnetic field is outputted to the position and direction calculating circuit 36 in a position and direction detecting portion 4B via a cable 33 connected to the receiving coils 51 and the receiving coil 52 for detecting the position and the direction.

According to the second embodiment, referring to FIG. 5, the position and direction detecting portion 4B has transmitting coils 53 in place of the receiving coils 37, and a coil driving circuit 35 applies a coil driving signal to the transmitting coils 53. As mentioned above, the magnetic field is detected by the receiving coils 51 and the receiving coil 52 for detecting the position and the direction.

Incidentally, according to the second embodiment, a white LED is arranged in the illuminating window 15 shown in FIG. 6 to emit light from the white LED and to output white illumination light from the illuminating window 15. Thus, the second embodiment needs no external light source device 7. Other constructions are the same as those according to the first embodiment.

Next, the operation will be described according to the second embodiment.

The coil driving circuit 35 in the position and direction detecting portion 4B outputs a coil energizing signal as an AC signal to the transmitting coils 53. Thus, alternating magnetic field is generated between the subject 8 and the distal end of the endoscope inserting portion 9.

The receiving coil 52 for detecting the position and the direction and the receiving coils 51 receive the magnetic field which is energized by the transmitting coils 53, and output the magnetic field detecting signals as the electrical signals to the position and direction detecting circuit 36.

The position and direction calculating circuit 36 calculates positional and directional data which is expressed on the coordinate system O-xyz fixed to the transmitting coils 53 of the receiving coil 52 for detecting the position and the direction and the receiving coils 51. Data is the same as that according to the first embodiment. Other operations are the same as those according to the first embodiment.

The second embodiment has the following advantages.

That is, with the construction and the operation according to the second embodiment, the coil which transmits the magnetic field is arranged outside the subject 8. As compared with the first embodiment, advantageously, the output of the magnetic field is increased, an S/N ratio of the reception is raised, and the accuracy of the positional and directional data is improved. Other advantages are the same as those according to the first embodiment.

Modification

The modifications described according to the first embodiment are applied to those according to the second embodiment.

Third Embodiment

Figure 7:
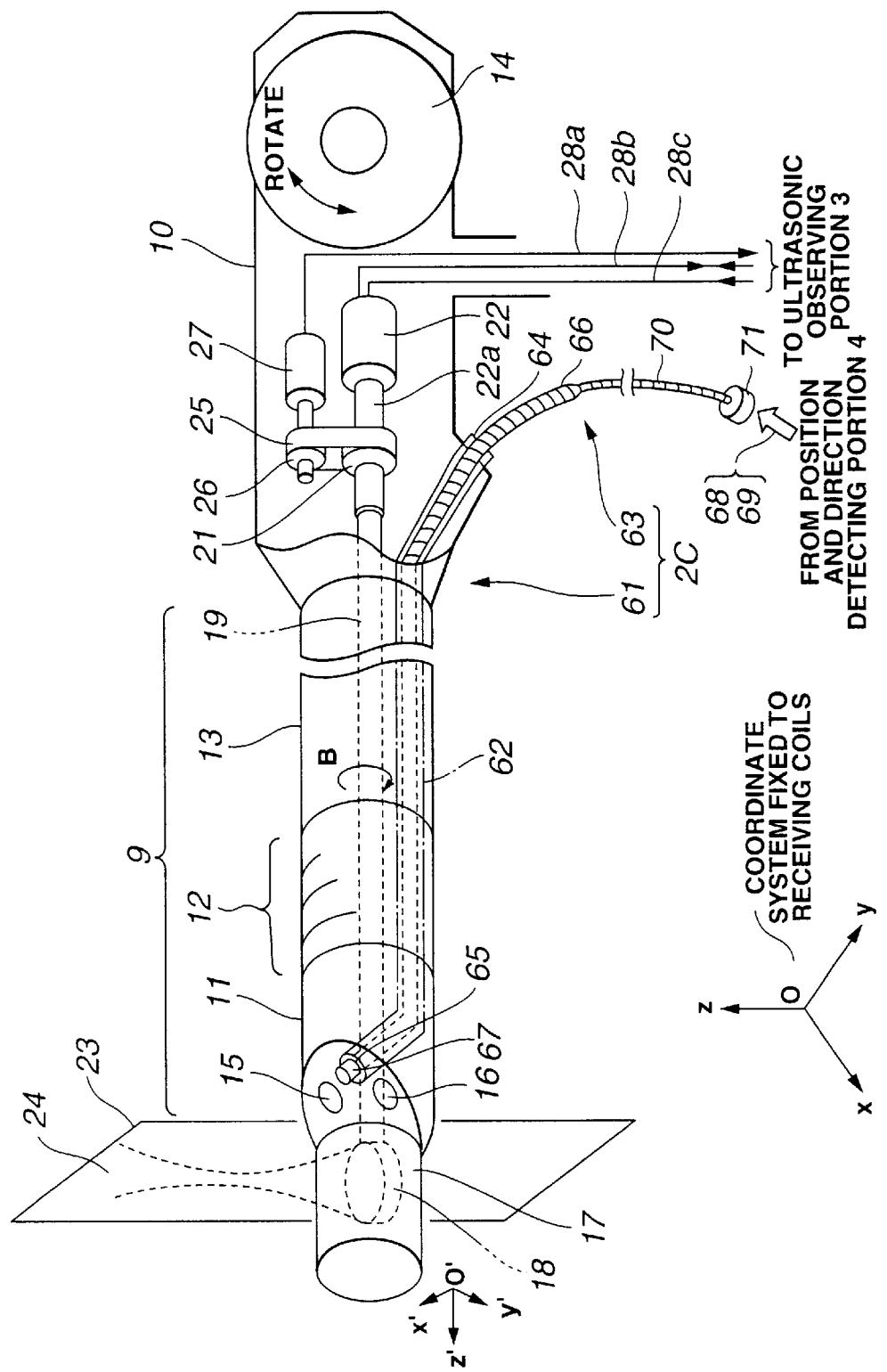
FIG. 7 is an explanatory diagram showing the structure of an ultrasonic endoscope according to a third embodiment of the present invention.
Figure 8:
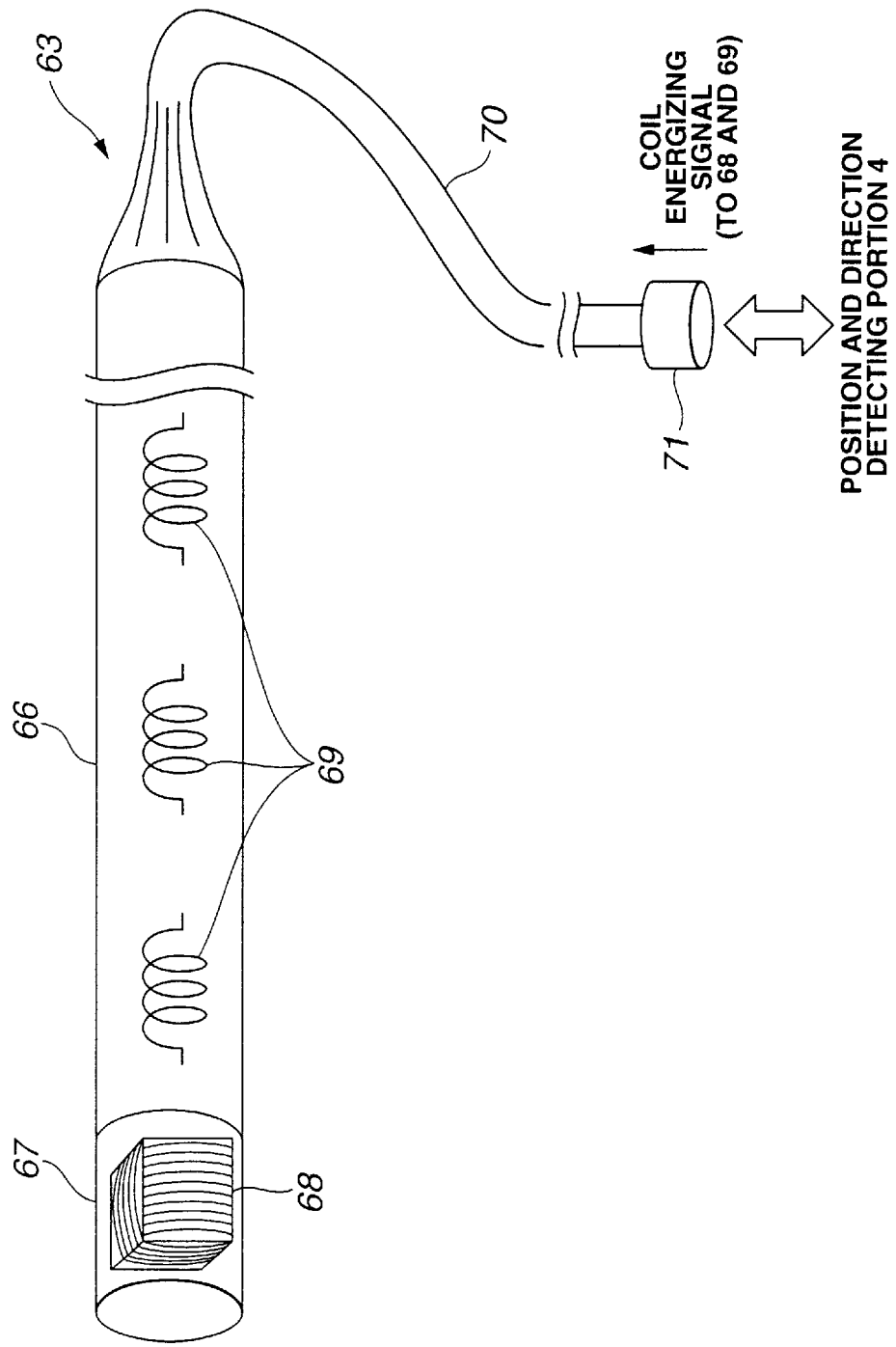
FIG. 8 is an explanatory diagram showing the structure of a detecting catheter.

Next, a description is given of a third embodiment of the present invention with reference to FIGS. 7 and 8. FIG. 7 shows the structure of an ultrasonic endoscope according to the third embodiment. FIG. 8 shows the structure of a detecting catheter.

An ultrasonic diagnostic apparatus according to the third embodiment of the present invention is different from the ultrasonic endoscope 2 shown in FIG. 1 according to the first embodiment, and uses an ultrasonic endoscope 2C shown in FIG. 7.

Basically, the ultrasonic endoscope 2C has the same functions as those of the ultrasonic endoscope 2 shown in FIG. 2 by inserting and attaching a detecting catheter 63 shown in FIG. 8 to a clamp channel 62 in an ultrasonic endoscope main body 61. Hereinbelow, only different portions are described.

Referring to FIG. 7, a clamp inserting slot 64 is set near the front end of the endoscope operating portion 10 in the ultrasonic endoscope main body 61. The clamp inserting slot 64 is tunnel-shaped along the longitudinal direction of the endoscope inserting portion 9 by a hollow tube and is thus connected to the clamp channel 62 for inserting a clamp, etc.

The clamp channel 62 is opened at a projecting slot 65 arranged at a slope portion having the illuminating window 15 of the distal end portion 11.

The ultrasonic endoscope main body 61 according to the third embodiment has the same structure as that of general ultrasonic endoscopes. Therefore, the ultrasonic endoscope main body 61 has neither the transmitting coils 31 nor the receiving coils 32 for detecting the position and the direction in the ultrasonic endoscope 2 shown in FIG. 2. In place thereof, the detecting catheter 63 shown in FIG. 8 is inserted and attached to the clamp channel 62 in the ultrasonic endoscope main body 61 and thus the ultrasonic endoscope has the same functions as those of the ultrasonic endoscope 2 shown in FIG. 2.

The detecting catheter 63 shown in FIG. 8 which is detachable to the clamp channel 62 in the ultrasonic endoscope main body 61 includes the hollow tube 66 made of a flexible material such as silicon tube, and a hard distal end housing 67 at the distal end of the tube 66.

A transmitting coil for detecting the position and the direction of the tomographic plane (hereinafter, referred to as a transmitting coil for detecting the position and the direction) 68 is accommodated and fixed in the distal end housing 67.

A plurality of transmitting coils for detecting the inserting shape (hereinafter, referred to as transmitting coils) 69 are arranged at a predetermined interval from the distal end to the proximal end of the tube 66, and they are fixed.

Coils 68 for detecting the position and the detecting and the transmitting coils 69 are connected to signal lines. A cable portion 70 which has a thin diameter from the proximal end of the tube 66 is inserted in the signal lines. The signal lines are connected to a connector 71 at the back end of the cable portion 70. The connector 71 is detachably connected to the position and direction detecting portion 4 (shown in FIG. 1), and is electrically connected to the coil driving circuit 35 in the position and direction detecting portion 4 so as to receive the coil energizing signal from the coil driving circuit 35 upon using.

The detecting catheter 63 is inserted in the clamp channel 62 from the clamp inserting slot of the ultrasonic endoscope main body 61, and only the distal end housing 67 at the distal end of the detecting catheter 63 is projected from the projecting slot 65 and is fixed by a fastening (not shown) in the clamp inserting slot 64. Other structures are the same as those according to the first embodiment.

Next, the operation will be described according to the third embodiment. upon examination using an ultrasonic endoscope 2C, the detecting catheter 63 is inserted in the clamp channel 62 from the clamp inserting slot 64 of the ultrasonic endoscope main body 61, and only the distal end housing 67 is projected at the projecting slot 65 and is fixed by a fastening (not shown) in the clamp inserting slot 64.

The coil driving circuit 35 in the position and direction detecting portion 4 (shown in FIG. 1) outputs the coil energizing signal as the AC signal to the transmitting coil 32 for detecting the position and the direction and the transmitting coils 31.

In the transmitting coil 32 for detecting the position and the direction, frequencies of the coil energizing signal are varied depending on the wiring directions. The frequency is different every transmitting coil 31. Alternating magnetic field is energized by varied frequencies depending on the directions of the transmitting coils 31 between the subject 8 and the distal end of the endoscope inserting portion 9.

With the above-mentioned structure and operation, the directions of the two solenoid coils of the transmitting coil 32 for detecting the position and direction completely do not match the three-o'clock direction (x' axis) and the twelve-o'clock direction (y' axis) of the ultrasonic tomogram. However, the position and direction calculating circuit 36 estimates and corrects the three-o'clock direction (x' axis) and the twelve-o'clock direction (y' axis) of the ultrasonic tomogram based on the magnetic field detecting signal indicating the direction of the transmitting coil 32 for detecting the position and the direction and a predetermined fixing method using the fastening at the inserting slot 64, and calculates the directional data ($\phi$, $\theta$, $\phi$). Other operations are the same as those according to the first embodiment.

The third embodiment has the following advantages.

That is, with the structure and operations according to the third embodiment, the transmitting coil 32 for detecting the position and the direction and the transmitting coils 31 are arranged to the detecting catheter 63, and are set independently of the ultrasonic endoscope main body 61. Thus, the concerning area is imaged in the ultrasonic tomogram for the diagnosis by inserting the detecting catheter 63 in the clamp channel 62 and referring to the auxiliary image upon imaging the concerning area. Upon processing after the diagnosis, processing tool such as the clamp is inserted after removing the detecting catheter 63 so as to perform various processing. Accordingly, the diagnosis and processing are smoothly executed by the single ultrasonic endoscope main body 61.

Further, with the structure and the operations, the transmitting coil 32 for detecting the position and direction and the transmitting coils 31 are set to the detecting catheter 63 (separately from the ultrasonic endoscope main body 61). As a result, the general ultrasonic endoscopes are used for the ultrasonic endoscope main body 61 and a dedicated ultrasonic endoscope fixedly having the transmitting coil 32 for detecting the position and the direction and the transmitting coils 31 is not necessarily bought. Other advantages are the same as those according to the first embodiment.

Modification

The third embodiment applies to the first embodiment, the construction in which the transmitting coil 32 for detecting the position and the direction and the transmitting coils 31 are independently arranged as the detecting catheter 63. However, it may apply the construction according to the second embodiment in which the reception and the transmission of the magnetic field are inverted. In other words, the third embodiment does not limit the relationship between the reception and the transmission of the magnetic field. Other modifications can be applied similarly to the above-described modifications according to the first embodiment.

Fourth Embodiment

Figure 9:
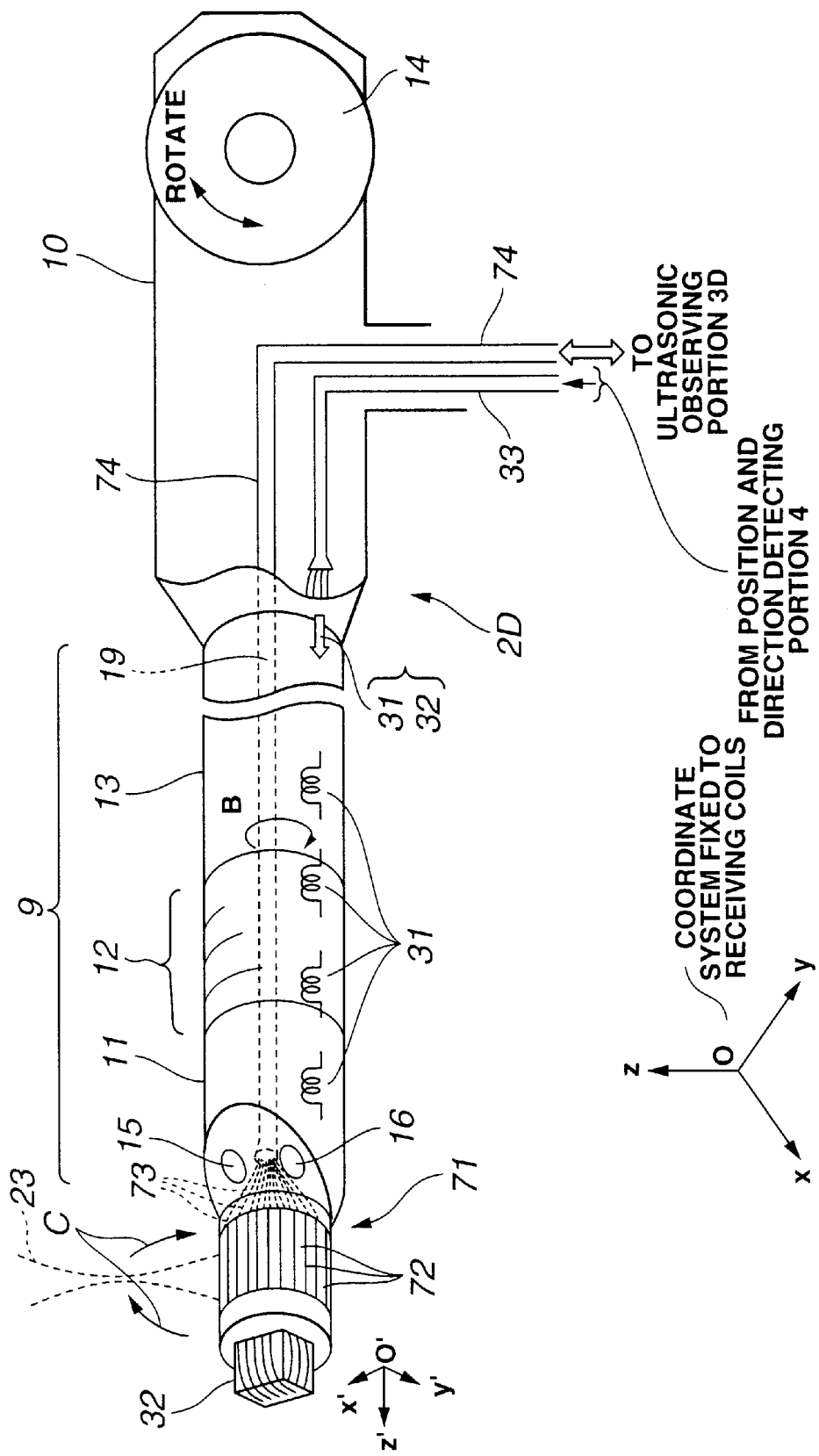
FIG. 9 is an explanatory diagram showing the structure of an ultrasonic endoscope according to a fourth embodiment of the present invention.
Figure 10:
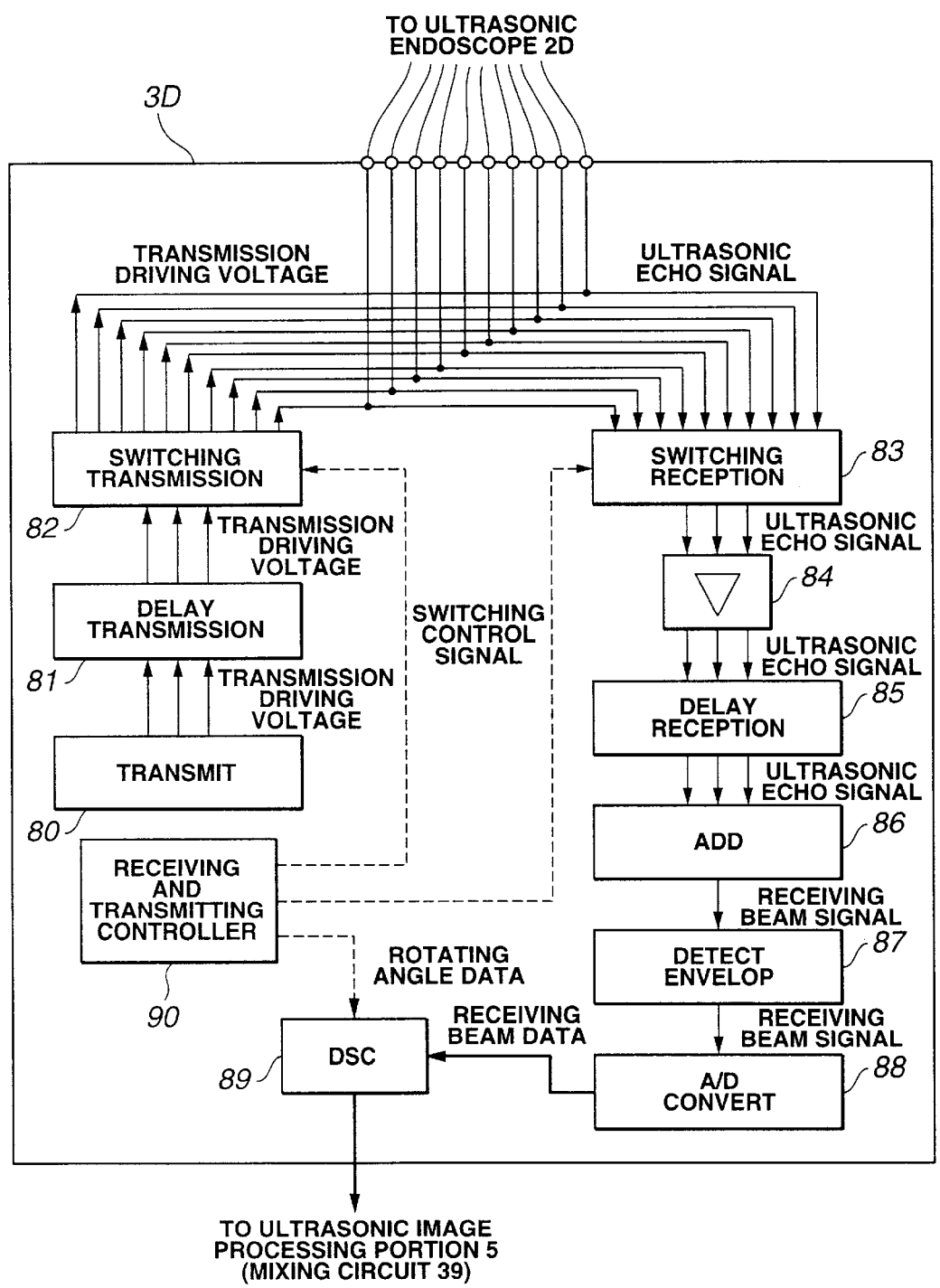
FIG. 10 is a block diagram showing the structure of an ultrasonic observing portion.

Next, a description is given of a fourth embodiment of the present invention with reference to FIGS. 9 and 10. FIG. 9 shows the construction of an ultrasonic endoscope. FIG. 10 shows the structure of an ultrasonic observing portion.

An ultrasonic diagnostic apparatus according to the fourth embodiment of the present invention is different from the structure of the ultrasonic endoscope 2 shown in FIG. 1 according to the first embodiment, and uses an electronic scanning ultrasonic endoscope 2D shown in FIG. 9 and an ultrasonic observing portion 3D shown in FIG. 10 having the structure different from that of the ultrasonic observing portion 3. Hereinbelow, only different portions are described.

Referring to FIG. 9, the ultrasonic endoscope 2D according to the fourth embodiment comprises a cylindrical (circular) ultrasonic vibrator array portion 71 in front of a slope portion having the illuminating window 15 and the observing window 16 at the distal end portion 11 of the distal end of the endoscope inserting portion 9.

A large number of strip ultrasonic vibrators 72 are arranged along a cylindrical plane thereof in the ultrasonic vibrator array portion 71. The ultrasonic vibrators 72 forming the ultrasonic vibrator array portion 71 are connected to signal lines 73. The signal lines 73 are bundled to become a cable 74, are inserted in the endoscope inserting slit 9 and the endoscope operating potion 10, and are connected to the ultrasonic observing portion 3D at the back end. Pulse transmission driving voltages (driving signals) are applied to the ultrasonic vibrators 72 from the ultrasonic observing portion 3D, the ultrasonic echo signal which is received by the ultrasonic vibrators 72 and is converted into the electrical signal is transferred to the ultrasonic observing portion 3D.

The transmitting coil 32 for detecting the position and the direction is attached to the front end of the ultrasonic vibrator array portion 71 in the distal end portion 11. The transmitting coils 31 are arranged at a predetermined interval in the longitudinal direction in the endoscope inserting portion 9. As described above according to the first embodiment, the coil energizing signal is applied to the transmitting coils 31 and the transmitting coil 32 for detecting the position and the detection from the position and direction detecting portion 4 via the cable 33.

According to the fourth embodiment, the ultrasonic vibrators 72 in the ultrasonic vibrator array portion 71 are driven on time series, thereby electronically radial-scanning ultrasonic beams 23 which are outputted. Reference numeral C in FIG. 9 denotes a radial-scanning direction.

Referring to FIG. 10, the ultrasonic observing portion 3D according to the fourth embodiment comprises: a transmitting circuit 80 which generates a pulse transmission driving voltage (driving signal) therein; a transmission delay circuit 81 which delays the transmission driving voltages varied depending on signal lines; a transmission switching circuit 82 which sequentially selects a plurality of ultrasonic vibrators 72 relating to the formation of the ultrasonic transmitting beams and which outputs the transmission driving voltage; a reception switching circuit 83 which sequentially selects the ultrasonic echo signals from the plurality of ultrasonic vibrators 72 relating to the formation of the transmitting beams and which outputs the selected signal to an amplifying circuit at the latter stage; an amplifying circuit 84 which amplifies the ultrasonic echo signals from the reception switching circuit 83; a reception delay circuit 85 which delays the amplified echo signals similarly to the delay operation of the transmission driving voltage in the transmission delay circuit 81; an adding circuit 86 which adds the delayed ultrasonic echo signals and which forms a receiving beam signal corresponding to a single sound ray; an envelope detecting circuit 87 which logarithm-amplifies the receiving beam signal and which detects an envelope of the reception beam signal; an A/D converting circuit 88 which A/D converts the envelope of the receiving beam signal and which converts the converted signal into receiving beam data, a digital scanning converter (hereinafter, simply referred to as a DSC) 89 which converts the receiving beam data on the polar coordinate system into data on the orthogonal coordinate system which can be outputted to the monitor 6; and a receiving and transmitting controller 90 which controls the circuits in the ultrasonic observing portion 3D.

The DSC 89 converts the receiving beam data on the polar coordinate system into the receiving data on the orthogonal coordinate system by rotating angle data from the receiving and transmitting controller 90, and outputs the converted data to the mixing circuit 39 in the ultrasonic image processing portion 5. Other structures are the same as those according to the first embodiment.

Next, the operation according to the fourth embodiment will be described.

A signal and data of the ultrasonic tomogram will be described.

The transmission driving voltage generated by the transmitting circuit 80 is properly delayed by the transmission delay circuit 81, and is inputted to the plurality of ultrasonic vibrators 72 which are selected by the transmission switching circuit 82. Then, the transmission switching circuit 82 selects the plurality of ultrasonic vibrators 72 which are continuously aligned by a switching control signal from the receiving and transmitting controller 90.

The transmission delay circuit 81 gives a large delay to the transmission driving voltage of the ultrasonic vibrator 72 in the center of the alignment, and a small delay to the transmission driving voltage as the ultrasonic vibrator 72 is far away from the center of the alignment. The ultrasonic vibrator 72 transduces the transmission driving voltages into the ultrasonic waves by electro-acoustic transducing. As a result of the delay operation, the single transmitting beam is formed from each of the ultrasonic waves.

The receiving and transmitting controller 90 enables the transmission switching circuit 82 to select the ultrasonic vibrator 72 via the switching control signal so that the ultrasonic beam is sequentially circled in a direction shown by an arrow indicating radial scan C in FIG. 9. Thus, the cross section vertical to the inserting axis of the ultrasonic endoscope 2D is scanned, that is, electronic radial scanning is performed.

The ultrasonic vibrator array portion 71 receives, transmits, and radially scans the ultrasonic signals. Then, the ultrasonic vibrator array portion 71 transduces the ultrasonic echo of the tomographic plane into an electrical signal, and outputs the ultrasonic echo signal to the reception switching circuit 83 in the ultrasonic observing portion 3D.

The switching control signal from the receiving and transmitting controller 90 enables the reception switching circuit 83 to select the same ultrasonic vibrators 72 as those selected by the transmission switching circuit 82, then, the ultrasonic echo signals from the selected ultrasonic vibrators 72 are outputted to the amplifying circuit 84. The ultrasonic echo signals are amplified by the amplifying circuit 84, are properly delayed by the reception delay circuit 85, and are added by the adding circuit 86. Consequently, a single ultrasonic receiving beam signal is formed.

The receiving beam signal is logarithm-amplified by the envelope detecting circuit 87, the envelope thereof is detected, and is digitally converted into the receiving beam data by the A/D converting circuit 88. After that, the converted signal is outputted to the DSC 89.

The receiving and transmitting controller 90 outputs the switching control signal to both the transmission switching circuit 82 and the reception switching circuit 83, based on information on which ultrasonic vibrator 72 is switched thereby. Further, the receiving and transmitting controller 90 outputs to the DSC 89, the rotating angle of the radial scanning of the ultrasonic vibrator array portion 71 as the rotating angle data.

The DSC 89 converts the receiving beam data on the polar coordinate system into the data on the orthogonal coordinate system based on the rotating angle data so that the receiving beam data is outputted to the monitor, forms image data of the ultrasonic tomogram, and outputs the formed data to the mixing circuit 39 in the ultrasonic image processing portion 5. Other operation is the same as that of the first embodiment.

The fourth embodiment has the following advantages.

That is, the fourth embodiment uses the ultrasonic endoscope 2D in which the ultrasonic vibrator array portion 71 is arranged at the distal end and the radial scanning is electrically performed and the ultrasonic tomogram is formed based on the rotating angle data from the receiving and transmitting controller 90. As compared with the construction according to the first embodiment in which the ultrasonic endoscope 2 for mechanical radial scanning via the flexible shaft 19 is used and in which the ultrasonic tomogram is formed by using the rotating angle signal detected by the rotary encoder 27 in the endoscope operating portion 10 away from the ultrasonic vibrator 18, the angle in the twelve-o'clock direction of the ultrasonic tomogram is more accurately obtained without influences such as an angle detecting error due to rotating angle deviation caused by twist at both ends of the flexible shaft 19 and due to angle deviation between the flexible shaft 19 and the transmitting coil 32 for detecting the position and the direction attached to the distal end of the endoscope inserting portion 9.

Further, as compared with the construction according to the first embodiment in which the ultrasonic endoscope 2 for mechanical radial scanning via the flexible shaft 19 is used and in which the ultrasonic tomogram is formed by using the rotating angle signal detected by the rotary encoder 19 in the endoscope operating portion 10 away from the ultrasonic vibrator 18, there is no influence of the disturbance of the magnetic field that is caused by the change of arrangement of a metal portion due to the rotation of the flexible shaft 19 or the ultrasonic vibrator 18 in the endoscope inserting portion 9. Consequently, the angle in the twelve-o'clock direction of the ultrasonic tomogram is more accurately obtained without the deterioration in accuracy of data on the position and the direction obtained by the position and direction detecting portion 4.

Thus, the twelve-o'clock direction of the obtained ultrasonic tomogram matches the direction of the vector $V_{12}$ obtained from the transmitting coil 32 for detecting the position and the direction with higher accuracy. Further, it is advantageous to more accurately display an angle in the twisting direction (direction rotating around the endoscope inserting axis) of the tomographic-plane marker shown as the parallelogram and the up-direction marker. Other advantages are the same as those according to the first embodiment.

Modification

The fourth embodiment uses the construction using the ultrasonic endoscope 2D for electrical scanning for the first embodiment. However, it may use the ultrasonic endoscope 2D for the construction according to the second embodiment in which the reception and the transmission of the magnetic field are inverted. Alternatively, it may use the ultrasonic endoscope 2D for the construction according to the third embodiment in which the transmitting coil 32 for detecting the position and the direction and the transmitting coil 31 are arranged to the detecting catheter separately from the ultrasonic endoscope 2D.

Although the fourth embodiment uses the ultrasonic endoscope 2D as the radial scanning ultrasonic endoscope for electrical radial scanning, the present invention may use other scanning methods such as sector scanning or linear scanning. Further, it is not limited to the forementioned ultrasonic wave scanning method and can be applied to a linear scanning method which is not vertical but in parallel with the endoscope inserting axis and a convex scanning method and the like. In addition, the circular ultrasonic vibrator array portion 71 is not necessarily arranged around the entire circumference of 360°, and it may be arranged at any angle, e.g., 270° and 180°.

The ultrasonic probe having no optical observing window 16 may be used. Although the tomographic plane of the radial scanning of the radial scanning ultrasonic endoscope is used as the scanning plane, various planes or curve planes may be used according to various scanning methods. In addition, the same modifications as those of the first embodiment can be applied.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic diagnostic apparatus for forming an ultrasonic tomogram based on an ultrasonic echo signal, comprising:

an ultrasonic probe having an ultrasonic vibrator at a distal end portion thereof, the ultrasonic vibrator designed to be inserted in the celom, the ultrasonic probe which outputs the ultrasonic echo signal;

an inserting shape detecting means which detects an inserting shape of the ultrasonic probe;

an auxiliary-image forming means which forms an auxiliary image correlating the inserting shape obtained by the inserting shape detecting portion with the ultrasonic tomogram;

an output means which outputs the ultrasonic tomogram and the auxiliary image to a display device so that they can be compared with each other; and a tomographic-plane position and direction detecting means which detects a position and a direction of a diagnostic plane obtained by the ultrasonic diagnostic apparatus, wherein the auxiliary-image forming means forms a tomographic plane marker indicating a position and a direction of the tomographic plane obtained by the tomographic-plane position and direction detecting means and which combines the tomographic plane marker and the inserting shape to form the auxiliary image.

2. The ultrasonic diagnostic apparatus according to claim 1, wherein the auxiliary-image forming means forms a directional marker indicating a specific direction of the tomogram, and combines the directional marker, the tomographic plane marker, and the inserting shape to form the auxiliary image.

3. The ultrasonic diagnostic apparatus according to claim 1, wherein the inserting shape detecting means and the tomographic-plane position and direction detecting means are arranged to a detecting catheter separately from the ultrasonic probe, and the detecting catheter is inserted in the ultrasonic probe.

4. The ultrasonic diagnostic apparatus according to claim 1, wherein the ultrasonic probe is an electronic scanning ultrasonic probe having an ultrasonic vibrating array at a distal end portion thereof.

5. The ultrasonic diagnostic apparatus according to claim 1, wherein the inserting shape detecting portion detects an inserting shape by magnetic field.

6. The ultrasonic diagnostic apparatus according to claim 1, wherein the tomographic-plane position and direction detecting means detects the position and the direction of the tomogram by using magnetic field.

7. The ultrasonic diagnostic apparatus according to claim 1, wherein said tomographic-plane position and direction detecting means comprises a transmitting coil.

8. An ultrasonic diagnostic apparatus comprising:

an inserting means having an optical observing portion at a distal end portion thereof, which is designed to be inserted in the celom;

an ultrasonic vibrator which is connected to a flexible shaft and which can be arranged at the distal end portion;

an ultrasonic tomogram generating means which forms an ultrasonic diagnostic image based on an ultrasonic echo signal outputted from the ultrasonic vibrator;

an inserting shape detecting means which detects an inserting shape of the inserting portion;

an auxiliary-image forming means which forms an auxiliary image correlating the ultrasonic diagnostic image with the inserting shape obtained by the inserting shape detecting means;

an output means which outputs the ultrasonic image and the auxiliary image to a display device so that they can be compared with each other; and a tomographic-plane position and direction detecting means which detects a position and a direction of a diagnostic plane obtained by the ultrasonic diagnostic apparatus, wherein the auxiliary-image forming means forms a tomographic plane marker indicating a position and a direction of the tomographic plane obtained by the tomographic-plane position and direction detecting means and which combines the tomographic plane marker and the inserting shape to form the auxiliary image.

9. The ultrasonic diagnostic apparatus according to claim 8, wherein said tomographic-plane position and direction detecting means comprises a transmitting coil.

10. An ultrasonic diagnostic apparatus for forming an ultrasonic tomogram based on an ultrasonic echo signal, comprising:

an ultrasonic probe having an ultrasonic vibrator at a distal end portion thereof, which is designed to be inserted in the celom;

an inserting shape detecting portion which detects an inserting shape of the ultrasonic probe;

an auxiliary-image forming portion which forms an auxiliary image correlating the ultrasonic tomogram with the inserting shape obtained by the inserting shape detecting portion;

an output portion which outputs the ultrasonic tomogram and the auxiliary image to a display device so that they can be compared with each other; and a tomographic-plane position and direction detecting portion which detects a position and a direction of a diagnostic plane obtained by the ultrasonic diagnostic apparatus, wherein the auxiliary-image forming portion forms a tomographic plane marker indicating a position and a direction of the tomographic plane based on the position and the direction of the tomographic plane obtained by the tomographic-plane position and direction detecting portion, and forms the auxiliary image by combining the tomographic plane marker and the inserting shape.

11. The ultrasonic diagnostic apparatus according to claim 10, wherein the auxiliary-image forming portion forms a directional marker indicating a specific direction of the tomogram, and forms the auxiliary image by combining the directional marker, the tomographic plane marker, and the inserting shape.

12. The ultrasonic diagnostic apparatus according to claim 10, wherein the inserting shape detecting portion and the tomographic-plane position and direction detecting portion are arranged to a detecting catheter independently of the ultrasonic probe, and the detecting catheter is inserted in the ultrasonic probe.

13. The ultrasonic diagnostic apparatus according to claim 10, wherein the ultrasonic probe is an electronic scanning ultrasonic probe having an ultrasonic vibrating array at the distal end portion thereof.

14. The ultrasonic diagnostic apparatus according to claim 10, wherein the inserting shape detecting portion detects the inserting shape by using magnetic filed.

15. The ultrasonic diagnostic apparatus according to claim 10, wherein the tomographic-plane position and direction detecting portion detects the position and the direction of the tomogram by using magnetic field.

16. The ultrasonic diagnostic apparatus according to claim 10, wherein said tomographic-plane position and direction detecting portion comprises a transmitting coil.

17. An ultrasonic diagnostic apparatus comprising:
- an inserting portion having an optical observing portion at a distal end portion thereof, which is designed to be inserted in the celom;
- an ultrasonic vibrator which is connected to a flexible shaft and can be arranged at the distal end portion;
- an ultrasonic tomogram generating portion which forms an ultrasonic tomogram based on an ultrasonic echo signal outputted from the ultrasonic vibrator;
- an inserting shape detecting portion which detects an inserting shape of the inserting portion;
- an auxiliary-image forming portion which forms an auxiliary image which correlates the ultrasonic diagnostic image with the inserting shape obtained by the inserting shape detecting portion;
- an output portion which outputs the ultrasonic diagnostic image and the auxiliary image to a display device so that they can be compared with each other; and
- a tomographic-plane position and direction detecting portion which detects a position and a direction of a diagnostic plane obtained by the ultrasonic diagnostic apparatus,
- wherein the auxiliary-image forming portion forms a tomographic plane marker indicating a position and a direction of the tomographic plane based on the position and the direction of the tomographic plane obtained by the tomographic-plane position and direction detecting portion, and forms the auxiliary image by combining the tomographic plane marker and the inserting shape.

18. An ultrasonic diagnostic method for forming an ultrasonic tomogram based on an ultrasonic echo signal outputted from an ultrasonic probe, the ultrasonic probe designed to be inserted in the celom and having an ultrasonic vibrator at a distal end thereof, the ultrasonic diagnostic method comprising:
- an inserting shape detecting step of detecting an inserting shape of the ultrasonic probe;
- an auxiliary-image forming step of forming an auxiliary image which correlates the ultrasonic tomogram with the inserting shape obtained in the inserting shape detecting step;
- an output step of outputting the ultrasonic tomogram and the auxiliary image to a display device so that they can be compared with each other; and
- a tomographic-plane position and direction detecting step of detecting a position and a direction of a diagnostic plane obtained in the ultrasonic diagnostic method,
- wherein in the auxiliary-image forming step, a tomographic plane marker indicating a position and a direction of a tomographic plane is formed based on the position and the direction of the tomographic plane obtained in the tomographic-plane position and direction detecting step, and the auxiliary image is formed by combining the tomographic plane marker and the inserting shape.

19. The ultrasonic diagnostic method according to claim 18, wherein in the auxiliary-image forming step, a directional marker indicating a specific direction of the tomogram is formed, and the auxiliary image is formed by combining the directional marker, the tomogram marker, and the inserting shape.

20. An ultrasonic diagnostic method for ultrasonic diagnostic by including an inserting portion having an optical observing portion at a distal end portion thereof, which is designed to be inserted in the celom, and an ultrasonic vibrator which is connected to a flexible shaft and can be arranged at the distal end portion, the ultrasonic diagnostic method comprising:
- an ultrasonic tomogram generating step of forming an ultrasonic tomogram based on an ultrasonic echo signal outputted from the ultrasonic vibrator;
- an inserting shape detecting step of detecting an inserting shape of the inserting portion;
- an auxiliary-image forming step of forming an auxiliary image which correlates the ultrasonic diagnostic image with the inserting shape obtained in the inserting shape detecting step;
- an output step of outputting the ultrasonic diagnostic image and the auxiliary image to a display device so that they can be compared with each other; and
- a tomographic-plane position and direction detecting step of detecting a position and a direction of a diagnostic plane obtained in the ultrasonic diagnostic method,
- wherein in the auxiliary-image forming step, a tomographic plane marker indicating a position and a direction of a tomographic plane is formed based on the position and the direction of the tomographic plane obtained in the tomographic-plane position and direction detecting step, and the auxiliary image is formed by combining the tomographic plane marker and the inserting shape.

* * * * *